(12) United States Patent
Chang et al.

(10) Patent No.: US 8,980,128 B2
(45) Date of Patent: *Mar. 17, 2015

(54) ADSORBENT FOR WATER ADSORPTION AND DESORPTION

(75) Inventors: Jong-San Chang, Daejeon (KR); Sung-Hwa Jhung, Daejeon (KR); Young-Kyu Hwang, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 43 days.

This patent is subject to a terminal disclaimer.

(21) Appl. No.: 13/155,907

(22) Filed: Jun. 8, 2011

(65) Prior Publication Data

US 2011/0236298 A1     Sep. 29, 2011

Related U.S. Application Data

(62) Division of application No. 12/282,099, filed as application No. PCT/KR2007/001122 on Mar. 7, 2007, now abandoned.

(30) Foreign Application Priority Data

Mar. 10, 2006    (KR) ...................... 10-2006-0022809
Dec. 2, 2006     (KR) ...................... 10-2006-0121071

(51) Int. Cl.

| | | |
|---|---|---|
| *C09K 3/00* | (2006.01) | |
| *B01J 20/22* | (2006.01) | |
| *B01J 20/02* | (2006.01) | |
| *B01J 20/28* | (2006.01) | |
| *B01J 20/30* | (2006.01) | |
| *B01J 20/32* | (2006.01) | |
| *C07F 11/00* | (2006.01) | |
| *B01D 53/26* | (2006.01) | |
| *B01D 53/28* | (2006.01) | |

(52) U.S. Cl.
CPC ............... *B01J 20/226* (2013.01); *B01J 20/02* (2013.01); *B01J 20/0214* (2013.01); *B01J 20/0218* (2013.01); *B01J 20/0229* (2013.01); *B01J 20/28066* (2013.01); *B01J 20/28076* (2013.01); *B01J 20/2808* (2013.01); *B01J 20/30* (2013.01); *B01J 20/3204* (2013.01); *B01J 20/3208* (2013.01); *B01J 20/3236* (2013.01); *B01J 20/3242* (2013.01); *B01J 20/3248* (2013.01); *B01J 20/3255* (2013.01); *C07F 11/005* (2013.01); *B01D 53/263* (2013.01); *B01D 53/28* (2013.01); *B01J 20/28033* (2013.01); *B01D 2253/204* (2013.01); *B01D 2253/304* (2013.01); *B01D 2253/306* (2013.01); *B01D 2253/308* (2013.01); *B01D 2253/311* (2013.01); *B01J 2220/68* (2013.01)
USPC ........................................................ 252/194

(58) Field of Classification Search
USPC ........................................................ 252/194
See application file for complete search history.

(56) References Cited

U.S. PATENT DOCUMENTS

| | | | |
|---|---|---|---|
| 5,087,656 A | 2/1992 | Yoshinaga et al. | |
| 5,648,508 A * | 7/1997 | Yaghi | .................. 556/9 |
| 6,599,989 B2 | 7/2003 | Wada et al. | |
| 6,675,601 B2 | 1/2004 | Ebara | |
| 6,896,980 B2 | 5/2005 | Takahashi et al. | |
| 6,959,875 B2 | 11/2005 | Yabu et al. | |
| 6,964,998 B2 | 11/2005 | Wada et al. | |
| 6,978,635 B2 | 12/2005 | Yabu et al. | |
| 7,855,299 B2 * | 12/2010 | Jhung et al. | ...................... 556/44 |
| 2003/0004364 A1 | 1/2003 | Yaghi et al. | |
| 2003/0222023 A1 * | 12/2003 | Mueller et al. | ................ 210/656 |
| 2004/0225134 A1 | 11/2004 | Yaghi et al. | |
| 2006/0210458 A1 * | 9/2006 | Mueller et al. | ................. 422/231 |
| 2007/0248852 A1 * | 10/2007 | Mueller et al. | ................... 429/17 |
| 2009/0131643 A1 | 5/2009 | Ni et al. | |
| 2010/0132547 A1 * | 6/2010 | Masel et al. | ...................... 95/90 |

FOREIGN PATENT DOCUMENTS

| | | |
|---|---|---|
| JP | 10251530 A | 9/1998 |
| JP | 11335574 A | 12/1999 |
| JP | 2001259417 A | 9/2001 |
| JP | 2004103514 A | 4/2004 |
| JP | 20058204 A | 1/2005 |
| JP | 200595883 A | 4/2005 |
| JP | 200643567 A | 2/2006 |

(Continued)

OTHER PUBLICATIONS

Jhung et al. Microwave Synthesis of a Nanoporous Hybrid Material, Chromium Trimesate. Bull. Korean Chem Soc. 2005, vol. 26, No. 6, 88-881.*
Kitagawa et al.; "Functional Porous Coordination Polymers"; Angew. Chem. Int. Ed.; 2004; pp. 2334-2375; vol. 43; Wiley-VCH Verlag GmbH & Co. KGaA, Weinheim.
James; "Metal-Organic Frameworks"; Chem. Soc. Rev.; 2003; pp. 276-288; vol. 32.
Ferey et al.; "Crystallized Frameworks with Giant Pores: Are There Limits to the Possible?"; Accounts of Chemical Research; 2005; pp. 217-225; vol. 38; No. 4.
Rosseinsky; "Recent Developments in Metal-Organic Framework Chemistry: Design, Discovery, Permanent Porosity and Flexibility"; Microporous and Mesoporous Materials; 2004; pp. 15-30; vol. 73.

(Continued)

*Primary Examiner* — Harold Pyon
*Assistant Examiner* — Tanisha Diggs
(74) *Attorney, Agent, or Firm* — The Webb Law Firm (57) ABSTRACT

The present invention relates to methods for absorbing and/or desorbing water by contacting water with hybrid inorganic-organic material having high surface area, and pores with the size of molecules or nanometers. More specifically, the water adsorbent has facile adsorption-desorption even below 100° C., having high adsorption capacity, and having high desorption capacity when it is heated up to the temperature below 100° C. The adsorbent of the present invention can be applied to a humidifier, dehumidifier, cooler and heater. The present invention also relates to a technology to control humidity using the adsorbent.

13 Claims, 4 Drawing Sheets

(56) References Cited

FOREIGN PATENT DOCUMENTS

| KR | 20020048234 A | | 6/2002 |
|---|---|---|---|
| KR | 20050099239 | * | 10/2005 |
| KR | 1020060122576 A | | 11/2006 |
| WO | 2004069915 A2 | | 8/2004 |
| WO | WO 2005049484 | * | 6/2005 |
| WO | 2007044473 A2 | | 4/2007 |
| WO | 2007091828 A1 | | 8/2007 |
| WO | 2008066293 A1 | | 6/2008 |

OTHER PUBLICATIONS

Hermes et al.; "Selective Nucleation and Growth of Metal-Organic Open Framework Thin Films on Patterned COOH/CF3-Terminated Self-Assembled Monolayers on Au(111)"; J. Am. Chem. Soc.; 2005; pp. 13744-13745; vol. 127.

Kim et al.; "Morphology Control of Organic-Inorganic Hybrid Mesoporous Silica by Microwave Heating"; Chemistry Letters; 2004; pp. 422-423; vol. 33, No. 4.

Di Renzo; "Zeolites as Tailor-Made Catalysts: Control of the Crystal Size"; Catalysis Today; 1998; pp. 37-40; vol. 41.

Ferey et al.; "A Chromium Terephthalate-Based Solid with Unusually Large Pore Volumes and Surface Area"; Materials and Methods; Jun. 17, 2005; 3 pages.

Tosheva et al.; "Nanozeolites: Synthesis, Crystallization Mechanism, and Applications"; Laboratoire de Materiaux a Porosite Controlee, UMR-7016 CNRS, ENSCMu, Universite de Haute Alsace, 3, rue Alfred Werner, 68093; Mulhouse Cedex, France, 20 pages, 2005.

Park et al.; "Supramolecular Interactions and Morphology Control in Microwave Synthesis of Nanoporous Materials"; Catalysis Surveys from Asia; Jun. 2004; pp. 91-110; vol. 8; No. 2; Korea Research Institute of Chemical Technology; Taejon, Korea.

You et al.; "Liquid-Phase Catalytic Degradation of Polyethylene Wax Over MFI Zeolites with Different Particle Sizes"; Polymer Degradation and Stability; 2000; pp. 365-371; vol. 70; Chonnam National University, Kwangju, South Korea.

J. Sivaguru et al., "Achieving Enantio—and Diastereoselectivities in Photoreactions Through the Use of a Confined Space", Dep. Chem., Tulane Univ., New Orleans, LA 70118, USA, 2002.

Chen-Ho Tung et al., "Microreactor-controlled selectivity in organic photochemical reactions", Institute of Photographic Chemistry, Chinese Academy of Sciences, Beijing 100101, China, 2000, Pure Appl. Chem., vol. 72, No. 12, pp. 2289-2298.

N. Chen et al., Molecular Transport and Reaction in Zeolites (1994), "Zeolite Physical and Chemical Characteristics", pp. 17-18.

Jhung et al., "Microwave Synthesis of a Nanoporous Hybrid Material, Chromium Trimesate," Bull. Korean Chem. Soc., 2005, pp. 880-881, vol. 26, No. 6.

Serre et al., "Very Large Breathing Effect in the First Nanoporous Chromium(III)-Based Solids: MIL-53 or CRIII (OH)•{O2C-C6H4-CO2}•{HO2C-C6H4-CO2H}x•H2Oy," J. Am. Chem. Soc., 2002, pp. 13519-13526, vol. 124.

High-Capacity Methane Storage in Metal#Organic Frameworks M(dhtp): The Important Role of Open Metal Sites, Journal of the American Chemical Society, Article ASAP DOI: 10.1021/ja900258t, Publication Date (Web): Mar. 10, 2009, Downloaded from http://pubs.acs.org on Mar. 21, 2009.

* cited by examiner

ADSORBENT FOR WATER ADSORPTION AND DESORPTION

CROSS-REFERENCE TO RELATED APPLICATIONS

This application is a divisional application of U.S. application Ser. No. 12/282,099, filed Dec. 3, 2008 which is a national phase of International Patent Application No. PCT/KR2007/001122 filed Mar. 7, 2007, which claims priority to Korean Patent Application No. KR 10 2006 0022809 filed Mar. 10, 2006; and Korean Patent Application No. KR 10 2006 0121071 filed Dec. 2, 2006, all of which are incorporated herein by reference in their entireties.

TECHNICAL FIELD

The present invention relates to an adsorbent over which the adsorption and desorption processes of water are facile at the temperature of less than 100° C. and the difference between the adsorption capacity at adsorption condition and the adsorption capacity at desorption condition is high. More particularly, present invention relates to an adsorbent using porous inorganic-organic hybrid materials that have pores of nanometer-size and the pore volume and surface area are very large.

BACKGROUND ART

An adsorbent that adsorbs and desorbs water has various uses. For example, a dehumidifier can utilize an adsorbent that adsorbs water at low temperature, while desorbs water when it is heated at high temperature. Moreover, a heater may humidify like a humidifier by desorbing adsorbed water, at high temperature, which is adsorbed from outside environment at low temperature, if an adsorbent is used in a heater. Likewise, a cooler, if an adsorbent is incorporated, may decrease the humidity of a room by adsorbing water at low temperature. The adsorbed water may be desorbed to outside by heating at high temperature. Air conditioners and humidity controllers (humidistats) that utilized these concepts are suggested in U.S. Pat. Nos. 6,978,635, 6,959,875 and 6,675,601. However, there is no detailed explanation on the adsorbents used in the equipments. It is said that silica gels, zeolites or ion-exchangers are used in the equipments or it is just stated that adsorbents are used for the equipments. Moreover, the adsorbents have drawbacks of low adsorption capacity, and the desorption temperature is higher than 100° C., leading to the increase of operation costs.

Therefore, it is highly desirable to develop an adsorbent that desorbs water even at low temperature and the difference between adsorption capacity and the remaining water after desorption is large. However, there always remain problems of difficult desorption if the adsorption capacity is high; and the difference between adsorption capacity and the remaining water after desorption is small when the adsorption capacity is small. The present invention can be completed by confirming that, by utilizing a hybrid inorganic-organic material having very large surface area, the adsorption capacity is large and most of the adsorbed water can be desorbed at the temperature of 100° C. or below.

In the present invention, the hybrid inorganic-organic material, which is used as a water adsorbent, can be defined as a porous coordination compound formed by central metal ions and organic ligands that coordinate to the metal ions. The hybrid inorganic-organic material contains both organic species and inorganic species in the framework structure and means a crystalline compound having pore structure of molecular size or nano size. Hybrid inorganic-organic material is a wide terminology and generally called as porous coordination polymer (Angew. Chem. Intl. Ed., 43, 2334. 2004) or metal-organic frameworks (Chem. Soc. Rev., 32, 276, 2003). Recently, the study on these materials has been newly developed by the combination between molecular coordination bonds and materials science, and these materials have been actively investigated in these days because these materials, due to high surface area and pore of molecular dimensions or nanometers, can be used as versatile nanomaterials.

These materials can be synthesized by various methods. Typical synthesis methods include solvent diffusion at room temperature, hydrothermal synthesis at high temperature in the presence of water solvent and solvothermal synthesis using an organic solvent (Microporous Mesoporous Mater., 73, 15, 2004; Accounts of Chemical Research, 38, 217, 2005).

The synthesis of a hybrid inorganic-organic material can be executed, similar to the synthesis of inorganic porous materials including zeolites and mesoporous materials, under autogenous pressure in the presence of water or suitable solvents at temperature higher than the boiling point of the solvent used in the synthesis. In other words, the hybrid inorganic-organic material have been synthesized, similar to zeolites and mesoporous materials, during several days at high temperature after loading reactants in a high pressure reactor such as an autoclave. The heat source for high temperature has generally been conventional electric heating. For example, an autoclave containing precursors including metal salts, organic ligands and water or solvent was heated using an electric heater or an electric oven at a constant temperature. However, the methods of the previous embodiments using electric heating are not economical because of the long reaction time. Moreover, the methods do not provide hybrid inorganic-organic material with size less than 500 nm, or more preferably less than 100 nm, because amorphous hybrid inorganic-organic materials are obtained when the reaction duration is decreased in order to obtain small crystal particles.

Therefore, in the present invention, hybrid inorganic-organic materials are obtained by using microwave as a heat source in order to overcome the above mentioned problems. As small particles are obtained by microwave heating, the small particles, if used as an adsorbent, have the advantage of easy diffusion. Moreover, the small particles are easy to make a thin film, thick film or membrane. On the other hand, the synthesis by using microwave heating leads to improved performance of water adsorbent because the hydrophobicity and hydrophilicity of adsorbents are improved by the method. Therefore, hybrid inorganic-organic materials can be obtained by using microwave heating under the autogenous pressure after sealing the precursors containing metal salts, organic ligands and solvent such as water or organic solvent. Moreover, the hybrid inorganic-organic materials can be synthesized continuously by the microwave heating.

DISCLOSURE

Technical Problem

Accordingly, the object of this invention is to develop an adsorbent to have high adsorption capacity for water and to desorb easily the water at relative low temperature; and to develop an adsorbent, having outstanding adsorption capacity and adsorption characteristics, by using hybrid inorganic-organic materials. Therefore, the purpose of this invention is to develop an adsorbent that adsorb and desorb water easily, and has the purpose to control humidity by using the adsorbent thus obtained. Moreover, the present invention has another purpose to provide the preparation method of the adsorbent.

Technical Solution

The present invention is directed to a water adsorbent, especially to an adsorbent using porous hybrid inorganic-organic materials having pore dimension of nanometer levels.

The present invention provides an adsorbent by using hybrid inorganic-organic materials that desorb water easily even at low temperature and the difference between the adsorption capacity at high temperature and the adsorption capacity at low temperature is high.

The adsorbent according to the present invention has surface area larger than 1000 $m^2/g$, pore volume larger than 1.0 mL/g, pore dimension of 0.5-2.0 nm and the framework of the adsorbent is composed of both organic species and inorganic species. It is preferable for the adsorbent to have the ratio of (adsorption capacity at 100° C.)/(adsorption capacity at room temperature) is less than 0.2.

If the surface area and pore volume are less than the values described above, the efficiency as a water adsorbent is low. Even though the efficiency increases with increasing the surface area and pore volume, the practical limitations attainable by usual methods are about 10000 $m^2/g$ and 10 mL/g for surface area and pore volume, respectively. If the pore size is less than 0.5 nm, the time necessary for the adsorption and desorption is long because the adsorption and desorption velocities are low. On the contrary, if the pore size is larger than 2 nm, the structure of the adsorbent becomes unstable and the adsorbent has drawback of low stability.

Moreover, an adsorbent reported previously has drawback of inefficient desorption at low temperature because less than 500 of the adsorbed water is desorbed at the temperature of 100° C. or low and because the ratio of (adsorption capacity at 100° C.)/(adsorption capacity at room temperature) is 0.5-1.0. On the other hand, the adsorbent of the present invention desorbs, at the temperature of 100° C. or low, at least 80% of the adsorbed water.

The adsorbent of the present invention is specifically metal terephthalates or so, and the metal is Cr, Al, Fe, etc.

The preparation method of the present invention for the adsorbent is to add metal precursors, organic materials selected from benzene dicarboxylic acid, benzene tricarboxylic acids, etc. and solvents to a reactor; to seal the reactor; and to heat the reactor to high temperature. The reaction temperature is maintained by microwave heating, and the reaction pressure is maintained as autogenous pressure.

DESCRIPTION OF DRAWINGS

FIG. 1 and FIG. 2 are the SEM images for the chromium terephthalate obtained from Examples 1 and 3, respectively.

FIG. 3a and FIG. 3b are the XRD of chromium terephthalate obtained from Examples 2 and 3, respectively.

BEST MODE

The present invention will be described in more detail as follows:

The hybrid inorganic-organic material that is used as an adsorbent of the present invention is synthesized by the method including following steps:
1. Step to prepare reaction mixtures including mixing metal precursors, organic species that can be used as a ligand and solvents; and
2. Step to heat higher than 100° C. by irradiating microwave with frequency of 0.3-300 GHz.

The hybrid inorganic-organic materials obtained by the above method have pore dimension of nano levels and the particle size is homogeneous. The average particle size of the hybrid inorganic-organic materials is less than 500 nm, preferably, 10-500 nm, more preferably, 200 nm, more and more preferably, less than 100 nm, and most preferably, less than 50 nm. The hybrid inorganic-organic material obtained by the present invention is in the state of powder, thick film, thin film or membrane.

The membrane or thin film of porous hybrid inorganic-organic materials can be made by microwave irradiation after dipping a substrate in the reaction mixtures mentioned above.

The hybrid inorganic-organic materials according to the present invention is synthesized by microwave as a heat source, and any microwave having the frequency of 300 MHz-300 GHz is applicable to heat the reaction mixtures. Using microwave with the frequency of 2.45 GHz or 0.915 GHz, which is widely used commercially, is simple and effective.

Metallic species, one of the components of porous hybrid inorganic-organic materials, can be any metallic materials such as Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Mg, Ca, Sr, Ba, Sc, Y, Al, Ga, In, Tl, Si, Ge, Sn, Pb, As, Sb, and Bi. Transition metals, to make a coordination compound easily, are suitable for the invention. Among transition metals, Cr, Ti, V, Mn, Fe, Co, Ni and Cu are more suitable, and Cr is most suitable. Main group elements which make a coordination compound easily and lanthanides can also be used as metal components. Al and Si are suitable metallic components among main group elements, whereas Ce and La are suitable elements among lanthanides. As metallic precursors, metals themselves and any compounds containing metallic components can be used.

Another component of a hybrid inorganic-organic material is organic species and called linker. Any organic molecule is suitable as another component of a porous hybrid inorganic-organic material, a linker, as long as the molecule contains functional groups that can coordinate to a metal center. The functional groups that can coordinate to a metal are carboxylic acid, carboxylate, amino ($—NH_2$), imino, amide ($—CONH_2$), sulfonic acid ($—SO_3H$), sulfonate ($—SO_3^-$), methanedithionic acid ($—CS_2H$), methanedithionate ($—CS_2^-$), pyridine, pyrazine, etc. Multidentates, having multiple coordinating sites, such as bidentates and tridentates are suitable for preparing stable porous hybrid inorganic-organic materials. Any organic molecule can be used irrespective of the charges such as cationic, anionic and neutral compounds as long as they have coordination sites. For example, neutral molecules such as bipyridine and pyrazine and anionic molecules such as terephthalate, naphthalenedicarboxylate, benzenetricarboxylate, glutarate and succinate can be used. Ions containing aromatic rings such as terephthalate, ions without aromatic rings such as formate, and ions containing non-aromatic rings such as cyclohexyldicarboxylates are suitable for carboxylate anions. Not only organic species containing coordination sites but also organic species containing potential sites that can be transformed into a state suitable for coordination under the reaction conditions are applicable to organic precursors. For example, organic acids such as terephthalic acid can be used because it can be converted to terephthalate to coordinate to a metal center under reaction conditions. Typical organic species are benzenedicarboxylic acids, naphthalenedicarboxylic acids, benzenetricarboxylic acids, naphthalenetricarboxylic acids, pyridinedicarboxylic acids, bipyridyldicarboxylic acids, formic acid, oxalic acid, malonic acid, succinic acid, glutaric acid, hexanedionic acid, heptanedionic acid, cyclohexyldicarboxylic acids, etc. Anions of the above described acids are also suitable. Pyrazine and bipyridines are neutral species that can be applied as organic ligands. Mixtures of two or more of the above mentioned organic moieties are also applicable.

Chromium terephthalate, vanadium terephthalate and iron terephthalate are typical examples of porous hybrid inorganic-organic materials, and chromium terephthalate is one of the well-known porous hybrid inorganic-organic materials. Cubic chromium terephthalate with huge surface area and large pore size has great commercial interest and has high efficiency.

Instead of metallic components and organic ligands, suitable solvents are necessary for the synthesis of porous hybrid inorganic-organic materials. As the solvents, water, alcohols such as methanol, ethanol and propanol, and ketones such as acetone and methylethyl ketone and hydrocarbons such as hexanes, heptanes and octanes are suitable. Mixtures of above solvents can be applied and water is the most suitable solvent.

Sometimes, fluorine containing species such as HF are necessary for the synthesis of a hybrid inorganic-organic material, and ammonium fluoride, LiF, NaF, KF, CsF, etc. can be used. As the acidic conditions are generally preferable for the hybrid inorganic-organic materials synthesis, HF is preferable fluorine component.

The reaction temperature does not have any practical limitations. However, temperature above 100° C. is suitable, and temperature of 100-250° C. is more suitable, and temperature of 150-220° C. is most suitable. When the reaction temperature is too low, the reaction rate is too slow and the productivity is too low, whereas when the temperature is too high, dense species without pore are obtained and impurities can be byproduced because the reaction rate is too high. Moreover, it is costly to construct a reactor for high pressure reaction when the reaction temperature is too high. The reaction pressure does not have any limitation. It is convenient to perform a reaction under the autogenous pressure at the reaction temperature. Moreover, the reaction can be performed under increased pressure by adding inert gases such as nitrogen or helium.

The reaction can be carried out both in a batch mode and in a continuous mode. The batch mode operation is suitable for production in small scale because the throughput per time is low, whereas continuous mode is suitable for mass production of porous hybrid inorganic-organic materials even though investment cost is high. The reaction time of batch mode operation is from 1 min to 8 h. When the reaction time is too long, byproducts are mixed in the product and it is hard to get nanoparticles because of a crystal growth. On the contrary, the conversion is low when the reaction time is too short. Reaction time of 1 min-60 min is more suitable. The residence time of 1 min-60 min is suitable for the continuous reaction. When the residence time is too long, byproducts are mixed in the product and it is hard to get nanoparticles. The throughput per time is low when the residence time is long. On the contrary, reaction conversion is low when the residence time is short. The residence time of 1 min-20 min is more suitable. During the batch-mode reaction, the reaction mixtures can be agitated, and the agitation speed of 100-1000 rpm is suitable. The reaction can be performed statically and the static reaction is more suitable because of low investment cost and easy operability.

It is advisable to irradiate microwave on pretreated reaction mixtures because the reaction using microwave is very fast and homogeneous or nucleated reaction mixtures are suitable for the reaction. When the microwaves are irradiated on reaction mixtures without a pretreatment, the reaction rate is low or impurities may be mixed in or the crystal sizes can be inhomogeneous even though the process will be simple.

The pretreatment can be accomplished either by treatment using ultrasonics or by vigorous mixing. The pretreatment temperature is suitable between room temperature and the reaction temperature. If the pretreatment temperature is too low, the pretreatment effect is too small, whereas if the pretreatment temperature is too high, the equipment for pretreatment is complex and impurities may be byproduced. Pretreatment time longer than 1 min is suitable. Pretreatment time between 1 min and 5 h is more suitable for the ultrasonic treatment, whereas pretreatment for 5 min or more is more suitable for the vigorous stirring. If the pretreatment time is too short, the pretreatment effect is too small, whereas if the pretreatment time is too long, the efficiency of pretreatment is low. Pretreatment using ultrasonics is effective in pretreatment time and homogeneity of the reaction mixtures.

Moreover, a thick film, thin film and membrane of porous hybrid inorganic-organic materials can be made by microwave irradiation after dipping a substrate in the reaction mixtures mentioned above; and can be obtained, by a method using a binder including screen printing after preparation a hybrid inorganic-organic material. Thick films, thin films and membranes of porous hybrid inorganic-organic materials are necessary for the easy interaction between the adsorbent and water, and the performance of adsorption and desorption can be improved greatly by using them. The substrate can be alumina, silicon, glass, indium tin oxide (ITO), indium zinc oxide (IZO) and heat-resistant polymers. Any surface-treated substrate mentioned above will be more suitable.

The following specific examples are intended to be illustrative of the invention and should not be construed as limiting the scope of the invention as defined by appended claims.

Example 1

Cr-BDCA-1

Figure 1:
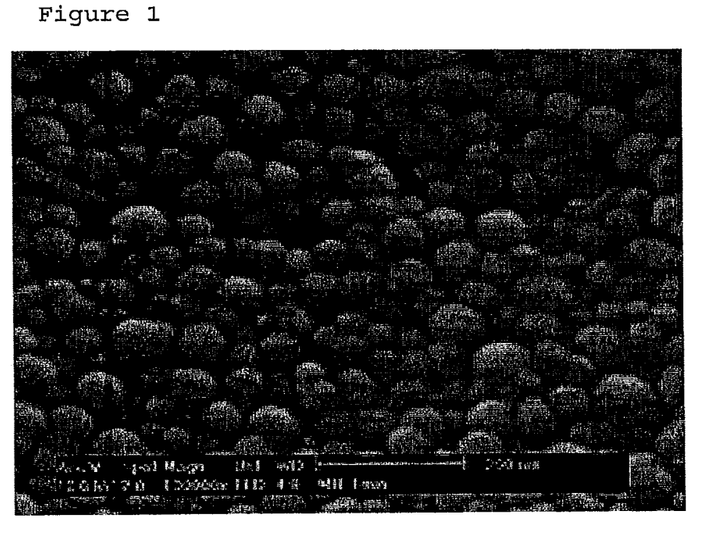
FIG. 1 and FIG. 2 represent the scanning electron microscope (SEM) images of chromium terephthalate, obtained in Examples.

Reaction mixtures with the molar composition of Cr:HF:BDCA:$H_2O$=1:1:1:275 were prepared from $Cr(NO_3)_3 \cdot 9H_2O$, aqueous HF, 1,4-benzenedicarboxylic acid (BDCA) and water. The reaction mixtures were loaded in a Teflon reactor, and pretreated by ultrasonication for 1 min in order to homogenize the mixture and facilitate the nucleation. The Teflon reactor containing pretreated reaction mixtures was put in a microwave oven (CEM, Mars-5). The synthesis was carried out under microwave irradiation (2.45 GHz) for 1 min at 210° C. after the reaction temperature was reached for 3 min under microwave irradiation. The porous hybrid inorganic-organic material, chromium terephthalate, Cr-BDCA-1 was recovered by cooling to room temperature, centrifugation, washing with deionized water and drying. It was confirmed that a cubic chromium terephthalate was obtained by the XRD result to show characteristic diffraction peaks at 3.3, 5.2, 5.9, 8.5 and 9. 1 (2θ). The SEM (scanning electron microscope) image of Cr-BDAC-1 obtained in this example is shown in FIG. 1, and shows that the crystals, having average pore size of 1.3 nm, are 30-40 nm and very homogeneous in size. These results show that a porous hybrid inorganic-organic material can be obtained very efficiently in a short reaction time by adequate pretreatment and microwave irradiation.

Example 2

Cr-BDCA-2

Figure 3:
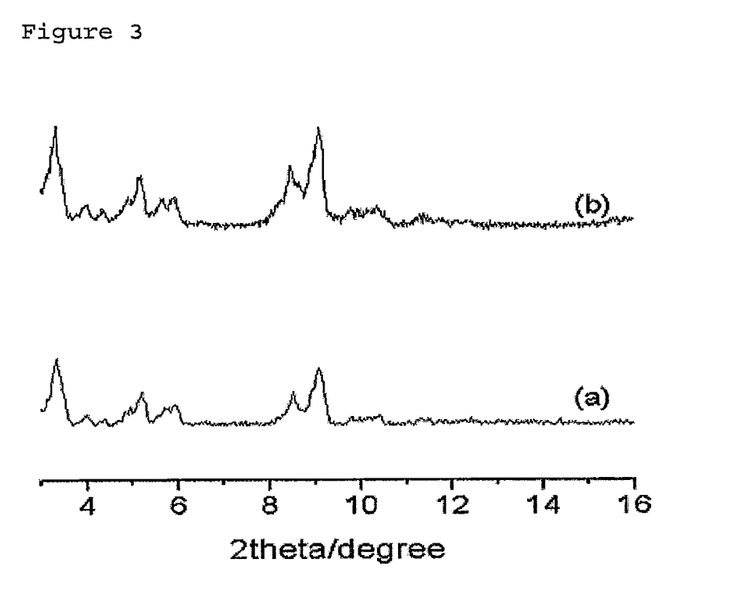
FIG. 3 represents the X-ray diffraction (XRD) patterns of chromium terephthalate, obtained in Examples.
Figure 4:
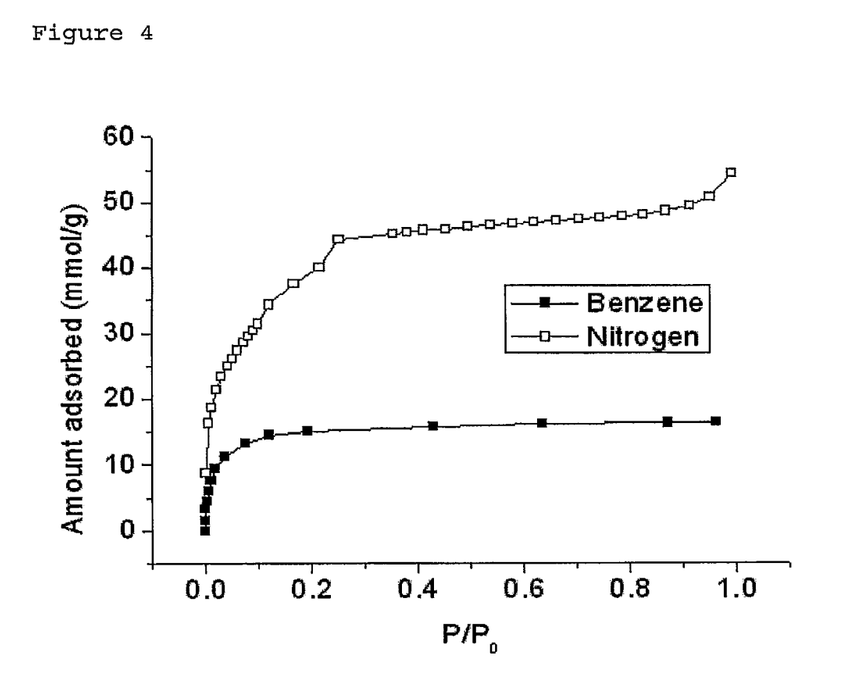
FIG. 4 represents the adsorption isotherms of nitrogen and benzene over chromium terephthalate, obtained in Example 2.

The synthesis of a porous hybrid inorganic-organic material was carried out as Example 1, except that ultrasonic pretreatment was omitted and the reaction time was 2 min. X-ray diffraction patterns of FIG. 3a show that a material with structure same as Example 1 was obtained, and SEM image confirms that a porous hybrid inorganic-organic material with homogeneous size of 40-50 nm was obtained. The porous hybrid inorganic-organic material, after evacuation at 150° C. under vacuum, has nitrogen adsorption capacity of 1050 mL/g or 46.9 mmol/g at relative pressure of 0.5 (P/Po=0.5, at liquid nitrogen temperature). Moreover, the porous hybrid inorganic-organic material has high benzene adsorption capacity (16 mmol/g) at 30° C. and relative pressure of 0.5 (P/Po=0.5). At this time, the average pore size of the hybrid inorganic-organic material is 1.3 nm. The adsorption isotherms of nitrogen and benzene are shown in FIG. 4.

The surface area and pore volume of the hybrid inorganic-organic material of this example are 3700 $m^2$/g and 1.9 mL/g, respectively. Therefore, the nanocrystalline porous hybrid inorganic-organic material, chromium terephthalate, synthesized in this example has very high adsorption capacity and crystalline porous material to be used successfully as adsorbents, catalysts, catalyst supports, etc.

Example 3

Cr-BDCA-3

Figure 2:
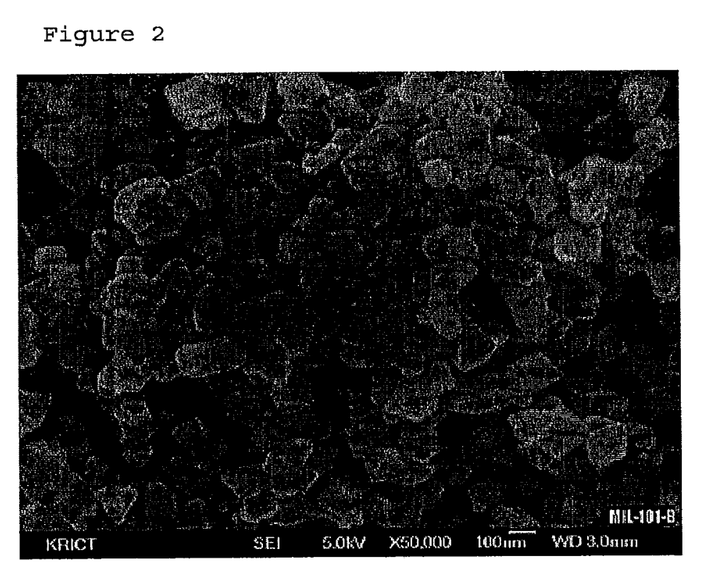

The synthesis of a porous hybrid inorganic-organic material was carried out as Example 2, except that the reaction time was 40 min. X-ray diffraction patterns of FIG. 3b show that a material with structure same as Example 1 was obtained, and SEM image (FIG. 2) confirms that a porous hybrid inorganic-organic material with homogeneous size of 200 nm was obtained even though the crystal size increased considerably compared with the size of Example 2. The surface area and pore volume of this material are 3900 $m^2$/g and 2.1 mL/g, respectively.

Example 4

Fe-BDCA-1

The synthesis of a porous hybrid inorganic-organic material was carried out as Example 2, except that $FeCl_3$ was used instead of $Cr(NO_3)_3 \cdot 9H_2O$. X-ray diffraction patterns showed that a material with structure same as Example 1 was obtained, and SEM image confirmed that a porous hybrid inorganic-organic material with homogeneous size of 50-100 nm was obtained.

Example 5

V-BDCA-1

The synthesis of a porous hybrid inorganic-organic material was carried out as Example 2, except that $VCl_3$ was used instead of $Cr(NO_3)_3 \cdot 9H_2O$. X-ray diffraction patterns showed that a material with structure same as Example 1 was obtained, and SEM image confirmed that a porous hybrid inorganic-organic material with homogeneous size of 50-80 nm was obtained.

Example 6

Cr-BDCA-1 Thin Film

Reaction mixtures with the molar composition of Cr:HF:BDCA:$H_2O$=1:1:1:275 were prepared from Cr $(NO_3)_3 \cdot 9H_2O$, aqueous HF, 1,4-benzenedicarboxylic acid (BDCA) and water. The reaction mixtures were loaded in a Teflon reactor, and an alumina plate was aligned vertically in the reaction mixture. The Teflon reactor containing reaction mixtures and alumina plate was put in a microwave oven (CEM, Mars-5). The synthesis was carried out under microwave irradiation (2.45 GHz) for 30 min at 210° C. after the reaction temperature was reached for 3 min under microwave irradiation. The porous hybrid inorganic-organic material, chromium terephthalate, Cr-BDCA-1 (both powder and thin film) was recovered by cooling to room temperature, centrifugation, washing with deionized water and drying. The XRD patterns of the thin film were very similar to those of experiment 3. These results show that a thin film of a porous hybrid inorganic-organic material can be obtained directly.

Example 7

Cr-BDCA: Characteristics of Water Adsorption and Desorption

Figure 5:
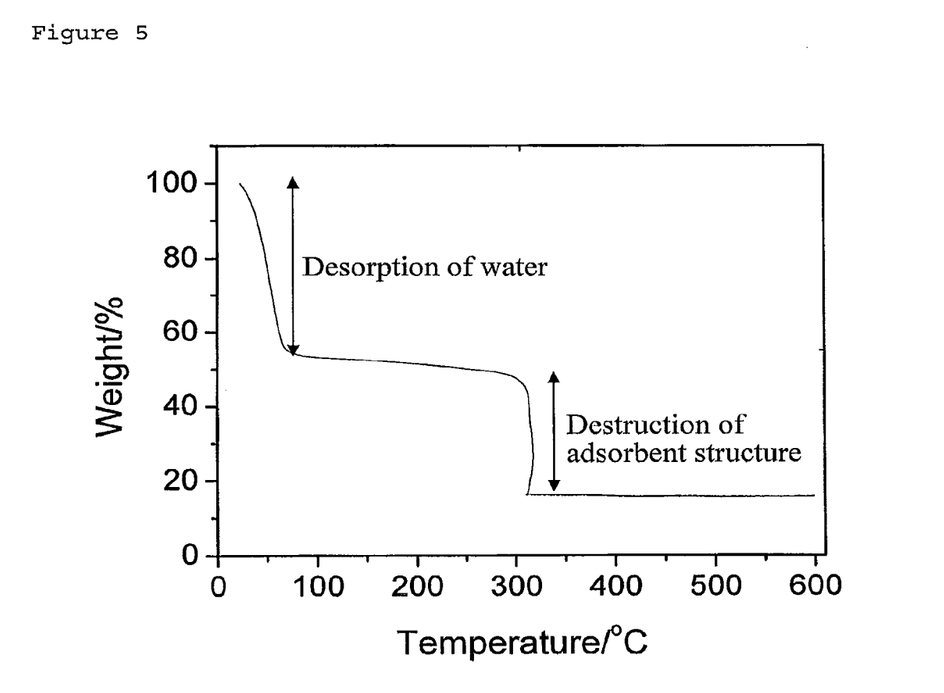
FIG. 5 represents the characteristics of water desorption from adsorbent made from chromium terephthalate, obtained in Example 3. The figure shows that the most of adsorbed water is desorbed at the temperature below 70° C.

The Cr-BDCA obtained in Ex. 3 was put in an upper part of a desiccator containing saturated ammonium chloride aqueous solution. The Cr-BDCA was remained for 3 days to fully adsorb water, and the amount of water desorption and desorption temperature were measured by using TGA (thermogravimetric analyzer). As shown in FIG. 5, water corresponding to about 37, 43, 45% of total weight is desorbed at 60, 65 and 70° C., respectively, and the mass reduction occurs above 300° C. by destruction of Cr-BDCA structure. As can be known from FIG. 5, the water adsorption capacity of Cr-BDCA is very high to show that about 45-50% of total weight of Cr-BDCA is water. Moreover, Cr-BDCA has high desorption capacity because more than 90% of the adsorbed water is desorbed at the temperature of 70° C. or low.

Example 8

Cr-BDCA: Experiment of Water Adsorption

The water adsorption experiment over Cr-BDCA obtained in Ex. 3 was carried out gravimetrically after drying at 150° C. under vacuum. The adsorption capacity based on the adsorbent weight at relative humidity of 21.4% was very low of 0.04 g/g. Therefore, it can be known that Cr-BDCA does not adsorb easily under the low humidity. It can be known that the Cr-BDCA will show excellent performance in humidifying and dehumidifying processes based on these characteristics and easy desorption at temperature of 100° C. or below.

Comparative Example 1

Water Adsorption and Desorption Characteristics Using Silica Gel

The water adsorption and desorption characteristics were analyzed as Example 7, except that silica gel was used instead of Cr-BDCA. The desorbed amount was just 15% at 70° C. and high temperature of 115° C. was necessary for water desorption of 30%.

INDUSTRIAL APPLICABILITY

As described above, the porous hybrid inorganic-organic material synthesized by the present invention has high water adsorption capacity and desorption capacity at low temperature of 100° C. or low, representing the applicability of the hybrid material in a dehumidifier, humidifier, cooler and heater. Especially, the operation cost of the equipments with the porous hybrid inorganic-organic material will be decreased much especially because of the low desorption temperature.

The invention claimed is:

1. A method for adsorbing and/or desorbing water, comprising:
contacting water with a hybrid inorganic-organic material that:
   a) is synthesized from a reaction between metal precursors and ligands selected from organic compounds; and
   b) has a surface area larger than 1000 m²/g; and
   c) has a pore dimension of 0.5 nm-2 nm,
   wherein the hybrid inorganic-organic material is homogeneous in particle size and has an average particle size of 10 nm to 500 nm, and
   wherein the organic compounds of the ligands are the molecules or molecular mixtures containing (i) an amide (—CONH$_2$) functional group, and (ii) optionally one or more functional groups selected from the group consisting of imino, carboxylic acid, carboxylate, amino (—NH$_2$), sulfonic acid (SO$_3$H), sulfonate (—SO$_3^-$), methanedithionic acid (—CS$_2$H), methanedithionate (—CS$_2^-$), pyridine and pyrazine.

2. The method according to claim 1, wherein the metal precursors are one or more of metals selected from Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Mg, Ca, Sr, Ba, Sc, Y, Al, Ga, In, Tl, Si, Ge, Sn, Pb, As, Sb and Bi; or metal compounds containing one or more components selected from Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Mg, Ca, Sr, Ba, Sc, Y, Al, Ga, In, Ti, Si, Ge, Sn, Pb, As, Sb and Bi.

3. The method according to claim 1, wherein the hybrid inorganic-organic material is in the state of thick film, thin film or membrane.

4. The method according to claim 3, wherein the hybrid inorganic-organic material in thick films, thin films or membranes are prepared by microwave heating after dipping alumina, silicon, glass, indium tin oxide (ITO), indium zinc oxide (IZO) or heat resistant polymers in the reaction mixtures; or after dipping the surface treated alumina, silicon, glass, indium tin oxide (ITO), indium zinc oxide (IZO) or heat resistant polymers in the reaction mixtures.

5. The method according to claim 1, wherein the hybrid inorganic-organic material is thick film, thin film or membrane prepared by microwave heating after dipping alumina, silicon, glass, indium tin oxide (ITO), indium zinc oxide (IZO) or heat resistant polymers in the reaction mixtures; or after dipping the surface treated alumina, silicon, glass, indium tin oxide (ITO), indium zinc oxide (IZO) or heat resistant polymers in the reaction mixtures.

6. The method according to claim 1, further comprising the step of heating the hybrid inorganic-organic material to a temperature of 100° C. or below to desorb at least a portion of the adsorbed water from the hybrid inorganic-organic material.

7. The method according to claim 6, wherein at least about 80% of the adsorbed water is desorbed from the hybrid inorganic-organic material.

8. The method according to claim 1, wherein the hybrid inorganic-organic material has a ratio of (adsorption capacity at 100° C.)/(adsorption capacity at room temperature) of less than 0.2.

9. A method of making a water adsorbent, comprising:
   a) mixing metal precursors, ligands and solvents to prepare a reactant mixture; and
   b) heating the reactant mixture at a temperature above about 100° C. to convert the reactant mixture to a hybrid inorganic-organic material that has a surface area larger than 1000 m²/g, and a pore dimension of 0.5 nm-2 nm,
   wherein the hybrid inorganic-organic material is homogenous in particle size and has an average particle size of 10 nm to 500 nm, and
   wherein the organic compounds of the ligands are the molecules or molecular mixtures containing (i) an amide (—CONH$_2$) functional group, and (ii) optionally one or more functional groups selected from the group consisting of imino, carboxylic acid, carboxylate, amino (—NH$_2$), sulfonic acid (SO$_3$H), sulfonate (—SO$_3^-$), methanedithionic acid (—CS$_2$H), methanedithionate (—CS$_2^-$), pyridine and pyrazine.

10. The method according to claim 9, wherein the reactant mixture is heated by microwave heating.

11. The method according to claim 9, further comprising pretreating the reactant mixture by ultrasonification or vigorous mixing prior to or during heating.

12. The method according to claim 9, further comprising applying a film or membrane of the hybrid inorganic-organic material to a substrate.

13. The method according to claim 9, further comprising applying the reactant mixture to a substrate and heating the reactant mixture to form the hybrid inorganic-organic material on the substrate.

* * * * *